(12) United States Patent
Nayak

(10) Patent No.: US 11,433,107 B2
(45) Date of Patent: *Sep. 6, 2022

(54) BACTERIAL COMPOSITIONS

(71) Applicant: Melaleuca, Inc., Idaho Falls, ID (US)

(72) Inventor: Subhendu Nayak, Ammon, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/804,458

(22) Filed: Feb. 28, 2020

(65) Prior Publication Data

US 2020/0197454 A1 Jun. 25, 2020

Related U.S. Application Data

(63) Continuation of application No. 14/986,854, filed on Jan. 4, 2016, now Pat. No. 10,576,112.

(60) Provisional application No. 62/099,410, filed on Jan. 2, 2015.

(51) Int. Cl.
*A61K 35/747* (2015.01)
*A61K 35/745* (2015.01)
*A61K 9/48* (2006.01)

(52) U.S. Cl.
CPC .............. *A61K 35/747* (2013.01); *A61K 9/48* (2013.01); *A61K 9/4866* (2013.01); *A61K 35/745* (2013.01)

(58) Field of Classification Search
None
See application file for complete search history.

(56) References Cited

U.S. PATENT DOCUMENTS

| | | | |
|---|---|---|---|
| 4,897,224 A | 1/1990 | Kondo et al. | |
| 5,502,045 A | 3/1996 | Miettinen et al. | |
| 6,008,027 A | 12/1999 | Langner | |
| 6,087,353 A | 7/2000 | Stewart et al. | |
| 6,333,047 B1 | 12/2001 | Katagihara et al. | |
| 6,441,206 B1 | 8/2002 | Mikkonen et al. | |
| 6,596,306 B1 | 7/2003 | Ho et al. | |
| 6,713,096 B2 | 3/2004 | Cho | |
| 6,818,233 B2 | 11/2004 | Perkes | |
| 6,964,969 B2 | 11/2005 | McCleary | |
| 7,138,149 B2 | 11/2006 | Cho | |
| 7,229,651 B2 | 6/2007 | Perkes | |
| 7,923,041 B2 | 4/2011 | Stock et al. | |
| 8,071,610 B2 | 12/2011 | Reynolds | |
| 8,168,170 B2 | 5/2012 | Matt | |
| 8,273,393 B2 | 9/2012 | Rabovsky et al. | |
| 8,491,939 B2 | 7/2013 | Rabovsky et al. | |
| 8,697,158 B2 | 4/2014 | Rabovsky et al. | |
| 8,722,035 B2* | 5/2014 | Porubcan | A61K 38/4873 424/93.3 |
| 8,747,915 B1 | 6/2014 | Giampapa | |
| 9,034,399 B2 | 5/2015 | Rabovsky et al. | |
| 9,179,693 B2 | 11/2015 | Romero et al. | |
| 9,210,945 B2 | 12/2015 | Horgan et al. | |
| 9,259,448 B2 | 2/2016 | Derrieu | |
| 10,576,112 B2* | 3/2020 | Nayak | A61K 9/48 |
| 11,207,388 B2 | 12/2021 | Rabovsky et al. | |
| 2004/0001817 A1 | 1/2004 | Giampapa | |
| 2004/0175389 A1 | 9/2004 | Porubcan | |
| 2004/0228931 A1 | 11/2004 | Chokshi et al. | |
| 2005/0032757 A1 | 2/2005 | Cho | |
| 2005/0069627 A1 | 3/2005 | Mysore et al. | |
| 2005/0244510 A1 | 11/2005 | Smith | |
| 2006/0153764 A1 | 7/2006 | Schumacher et al. | |
| 2006/0193842 A1 | 8/2006 | Porubcan | |
| 2007/0099986 A1 | 5/2007 | Ishichi | |
| 2007/0154575 A1 | 7/2007 | Shimoda et al. | |
| 2008/0181937 A1 | 7/2008 | Fotuhi | |
| 2009/0175936 A1 | 7/2009 | Rohr | |
| 2009/0175968 A1 | 7/2009 | Ivie et al. | |
| 2009/0181974 A1 | 7/2009 | Bourgeade et al. | |
| 2009/0263492 A1 | 10/2009 | Cashman et al. | |
| 2010/0166721 A1* | 7/2010 | Masri | A61K 35/745 424/93.44 |
| 2011/0008493 A1 | 1/2011 | Zorea | |
| 2011/0027418 A1 | 2/2011 | Horgan et al. | |
| 2011/0038848 A1 | 2/2011 | Rabovsky et al. | |
| 2011/0064720 A1 | 3/2011 | Amato | |
| 2011/0189132 A1 | 8/2011 | Garner et al. | |
| 2011/0206721 A1 | 8/2011 | Nair | |
| 2012/0009278 A1 | 1/2012 | Perry | |
| 2012/0034324 A1 | 2/2012 | Dubey | |
| 2012/0064051 A1 | 3/2012 | Mercenier et al. | |
| 2013/0216521 A1 | 8/2013 | Culver et al. | |
| 2014/0037582 A1 | 2/2014 | Romero et al. | |
| 2014/0322282 A1 | 10/2014 | Tuason et al. | |
| 2014/0370091 A1 | 12/2014 | Kikuchi et al. | |

(Continued)

FOREIGN PATENT DOCUMENTS

CN 1254256 5/2000
CN 1875094 12/2006

(Continued)

OTHER PUBLICATIONS

Bryan, et al., J. Nutr., 132:1345. (Year: 2002).

(Continued)

*Primary Examiner* — Vera Afremova
(74) *Attorney, Agent, or Firm* — Fish & Richardson P.C.

(57) ABSTRACT

This document provides bacterial compositions. For example, bacterial compositions having a combination of different bacterial strains formulated in a manner to maintain the stability of the bacteria are provided.

29 Claims, No Drawings

(56) References Cited

U.S. PATENT DOCUMENTS

| | | |
|---|---|---|
| 2015/0166466 A1 | 6/2015 | Kramer et al. |
| 2016/0193261 A1 | 7/2016 | Nayak |
| 2016/0193273 A1 | 7/2016 | Rabovsky et al. |
| 2016/0193306 A1 | 7/2016 | Rabovsky et al. |
| 2019/0167751 A1 | 6/2019 | Rabovsky |

FOREIGN PATENT DOCUMENTS

| | | |
|---|---|---|
| CN | 103193614 | 7/2013 |
| CN | 103524324 | 1/2014 |
| CN | 103664667 | 3/2014 |
| CN | 103880645 | 6/2014 |
| CN | 103951618 | 7/2014 |
| CN | 103976975 | 8/2014 |
| EP | 2520177 | 5/2017 |
| JP | 2013-530196 | 7/2013 |
| TW | 201431561 | 8/2014 |
| WO | WO 1999/007400 | 2/1999 |
| WO | WO 03/026687 | 4/2003 |
| WO | WO 2004/022031 | 3/2004 |
| WO | WO 2006/026713 | 3/2006 |
| WO | WO 2006/097043 | 9/2006 |
| WO | WO 2007/140621 | 12/2007 |
| WO | WO 2010/006173 | 1/2010 |
| WO | WO 2011/004375 | 1/2011 |
| WO | WO 2011/019867 | 2/2011 |
| WO | WO 2011/019875 | 2/2011 |
| WO | WO 2012/123770 | 9/2012 |
| WO | WO 2013/11100 | 8/2013 |
| WO | WO 2014/025905 | 2/2014 |
| WO | WO 2014/070014 | 5/2014 |
| WO | WO 2014/151329 | 9/2014 |
| WO | WO 2014/152236 | 9/2014 |
| WO | WO 2014/195741 | 12/2014 |
| WO | WO 2015/017625 | 2/2015 |
| WO | WO 2015/091365 | 6/2015 |

OTHER PUBLICATIONS

Di Meo, et al., J. Exp. Clin. Cancer Res., 38:360. (Year: 2019).
Lee, et al., Curr. Neuropharmacol., 11:338. (Year: 2013).
Memory Pro 2011 product listing, retrieved from the Wayback Machine, Internet Archive, (https://web.archive.org/web/20111025131756/http://pureencapsulations.com/itemdy00.asp?T1=MEP1). (Year: 2011).
Memory Pro, Dietary Supplement, Manufacturer: Pure Encapsulations®, Available on Amazon.com, https://vwvw.amazon.com/Pure-Encapsulations-Supplement-Broad-Spectrum-Capsules/dp/B01N9VLP1Z?ref_=ast_sto_dp#customerReviews. (Year: 2008).
Xu, et al., Acta Pharmacologice Sinica, 16:391. (Year: 1995).
U.S. Appl. No. 62/099,407, filed Jan. 2, 2015, Rabovsky et al.
Bassenge et al., "Dietary supplement with vitamin C prevents nitrate tolerance," J Clin Invest., 102(1):67-71, Jul. 1, 1998.
Bobko et al., "Trityl-based EPR probe with enhanced sensitivity to oxygen," Free Radic Biol Med., 47(5):654-658, Epub Jun. 10, 2009.
Dikalov et al., "ESR techniques for the detection of nitric oxide in vivo and in tissues," Methods Enzymol., 396:597-610, 2005.
Extended European Search Report in Application No. 16732905.1, dated Jun. 14, 2018, 9 pages.
Falbe, Ed., "Emulsions (HLB Values)," Surfactants in Consumer Products, 4.2.4 pp. 149-153, 1989.
Feuerstein et al., "Cytokines, inflammation, and brain injury: role of tumor necrosis factor-alpha," Cerebrovasc Brain Metab Rev., 6(4):341-360, Winter 1994.
Fink et al., "A new approach for extracellular spin trapping of nitroglycerin-induced superoxide radicals both in vitro and in vivo," Free Radic Biol Med., 28(1):121-128, Jan. 1, 2000.
International Preliminary Report on Patentability for International Application No. PCT/US2016/012060, dated Jul. 13, 2017, 8 pages.
International Preliminary Report on Patentability for International Application No. PCT/US2016/012063, dated Jul. 13, 2017, 7 pages.
International Preliminary Report on Patentability for International Application No. PCT/US2016/012091, dated Jul. 13, 2017, 7 pages.
International Search Report and Written Opinion for PCT/US2016/012060, dated May 2, 2016, 13 pages.
International Search Report and Written Opinion for PCT/US2016/012091, dated Mar. 17, 2016, 12 pages.
Komarov et al., "Electron paramagnetic resonance monitoring of ischemia-induced myocardial oxygen depletion and acidosis in isolated rat hearts using soluble paramagnetic probes," Magn Reson Med., 68(2):649-655, Epub Dec. 12, 2011.
Mrakic-Sposta et al., "Assessment of a standardized ROS production profile in humans by electron paramagnetic resonance," Oxid Med Cell Longev., vol. 2012 Article ID 973927, 10 pages, 2012.
Partial Supplementary European Search Report in Application No. 16732909.3, dated Jul. 25, 2018, 12 pages.
Pisaneschi et al., "Compensatory feto-placental upregulation of the nitric oxide system during fetal growth restriction," PLoS One, 7(9):e45294, Epub Sep. 27, 2012.
Purest Colloids, Inc., "Theralac Probiotic," Purest Colloids [online] copyright 2014 [retrieved on Dec. 18, 2014]. Retrieved from the Internet: <URL:www.purestcolloids.com/inside-theralac.php>, 2 pages.
Wikipedia, "Acetylcarnitine," Wikipedia.org [online] last modified Sep. 20, 2014. Retrieved from the Internet: <URL:http://en.wikipedia.org/wiki/Acetylcarnitine>. Retrieved on Nov. 19, 2014, 4 pages.
Wikipedia, "Curcumin," Wikipedia.org [online] last modified Nov. 7, 2014. Retrieved from the Internet: <URL: http://en.wikipedia.org/wiki/Curcumin>, retrieved on Nov. 20, 2014, 6 pages.
Wikipedia, "Huperzine A," Wikipedia.org [online], last modified Nov. 10, 2014. Retrieved from the Internet: <http://en.wikipedia.org/wiki/Huperzine_A>, 4 pages.
Wong et al., "Treatment of non-alcoholic steatohepatitis with probiotics. A proof-of-concept study," Annals Hepatol., 12(2):256-262, Mar. 1, 2013.
Wong et al., "Treatment of non-alcoholic steatohepatitis with probiotics. A proof-of-concept study," Annals of hepatology., 12(2):256-262, Mar. 1, 2013.
Uabundit et al., Journal of Ethnopharmacology, 127:26, 2010.

* cited by examiner

BACTERIAL COMPOSITIONS

CROSS-REFERENCE TO RELATED APPLICATIONS

This application is a continuation of U.S. application Ser. No. 14/986,854, filed on Jan. 4, 2016, which claims the benefit of U.S. Provisional Application No. 62/099,410 filed on Jan. 2, 2015, the contents of these aforementioned applications are hereby incorporated by reference.

BACKGROUND

1. Technical Field

This document relates to the field of bacterial compositions. For example, this document provides bacterial compositions having combinations of different bacterial strains formulated in a manner to maintain the stability of the bacteria.

2. Background Information

Consuming particular microorganisms in the form of a probiotic formulation can provide health benefits to mammals. There are hundreds of different bacterial strains within a human's digestive system. It is believed that some of these different bacteria help maintain a healthy digestive tract and help digest food.

Unfortunately, probiotic strains are extremely sensitive, and some strains may not be able to survive commercial production, storage, or gastrointestinal transit after consumption where they are exposed to heat, moisture, bile, low pH, and digestive enzymes. As a result, an undesirable reduction in the probiotic strain count occurs before the bacteria reach the intestine.

SUMMARY

This document provides bacterial compositions. For example, this document provides bacterial compositions having a combination of different bacterial strains formulated in a manner to maintain the stability of the bacteria. For example, the methods and materials provided herein can be used to deliver an effective and live dose of probiotics, to protect the probiotics during shelf life storage, and to achieve gastrointestinal bioavailability.

As described herein, a single bacterial composition (e.g., a capsule or tablet or sachet) can be formulated to include at least seven different bacterial strains, a form of silica (e.g., silica powder), fructooligosacchride, magnesium stearate, and a low moisture filler (e.g., a microcrystalline cellulose such as MCC 112) to provide a final composition with a water activity (Aw) less than 0.3 in a manner that helps maintain the stability of the bacteria within the composition and in a manner that delivers the bacteria to the intestines following oral administration. For example, at least about $1\times10^9$ colony forming units (CFUs) of each of *Lactobacillus acidophilus, Lactobacillus plantarum, Lactobacillus casei, Lactobacillus rhamnosus, Bifidobacterium longum, Bifidobacterium lactis,* and *Bifidobacterium bifidum* can be formulated with silica, fructooligosacchride, magnesium stearate, and a filler with a lower water content to form compositions with an $A_w$ less than 0.3 that maintain the viability of at least about 80 percent of the bacteria for at least about 12 months, at least about 18 months, or at least about 24 months, under standard storage conditions (e.g., room temperature under normal humidity).

As used herein, the term "about" when used to refer to weight % in a composition means±10% of the reported weight %. As used herein, the term "about" when used to refer to measured characteristics of the composition means±20% of the reported value.

The bacterial compositions provided herein can be coated with a coating agent and/or encapsulated to minimize or prevent moisture adsorption and to minimize water activity of the final blend.

In general, one aspect of this document features a bacterial composition comprising the bacteria *Lactobacillus acidophilus, Lactobacillus plantarum, Lactobacillus casei, Lactobacillus rhamnosus, Bifidobacterium longum, Bifidobacterium lactis,* and *Bifidobacterium bifidum,* wherein the bacterial composition releases the *Lactobacillus acidophilus, Lactobacillus plantarum, Lactobacillus casei, Lactobacillus rhamnosus, Bifidobacterium longum, Bifidobacterium lactis,* and *Bifidobacterium bifidum* within an intestine of a mammal following oral administration to the mammal, and wherein the composition has a water activity less than 0.3. For every gram of the composition, the composition can comprise between about $4\times10^9$ colony forming units and about $50\times10^9$ colony forming units of *Lactobacillus acidophilus*. For every gram of the composition, the composition can comprise between about $5\times10^9$ colony forming units and about $60\times10^9$ colony forming units of *Lactobacillus plantarum*. For every gram of the composition, the composition can comprise between about $4\times10^9$ colony forming units and about $50\times10^9$ colony forming units of *Lactobacillus casei*. For every gram of the composition, the composition can comprise between about $4\times10^9$ colony forming units and about $50\times10^9$ colony forming units of *Lactobacillus rhamnosus*. For every gram of the composition, the composition can comprise between about $2\times10^9$ colony forming units and about $40\times10^9$ colony forming units of *Bifidobacterium longum*. For every gram of the composition, the composition can comprise between about $4\times10^9$ colony forming units and about $50\times10^9$ colony forming units of *Bifidobacterium lactis*. For every gram of the composition, the composition can comprise between about $2\times10^9$ colony forming units and about $40\times10^9$ colony forming units of *Bifidobacterium bifidum*. The composition can comprise fructooligosaccharides. For every gram of the composition, the composition can comprise between about 0.5 mg and about 50 mg of fructooligosaccharides. The composition can comprise silicon dioxide. For every gram of the composition, the composition can comprise between about 5 mg and about 20 mg of silicon dioxide. The composition can comprise magnesium stearate. For every gram of the composition, the composition can comprise between about 10 mg and about 20 mg of magnesium stearate. For every gram of the composition, the composition can comprise more than $8\times10^9$ CFUs of bacteria. For every gram of the composition, the composition can comprise more than $10\times10^9$ CFUs of bacteria. For every gram of the composition, the composition can comprise more than $15\times10^9$ CFUs of bacteria. For every gram of the composition, more than $10\times10^9$ CFUs of bacteria of the composition remain viable after about 12 months of storage at room temperature and environmental humidity. For every gram of the composition, more than $10\times10^9$ CFUs of bacteria of the composition remain viable after about 12 months of storage at room temperature and environmental humidity. The *Lactobacillus acidophilus, Lactobacillus plantarum, Lactobacillus casei, Lactobacillus rhamnosus, Bifidobacterium longum, Bifidobacterium lactis,* and *Bifidobacterium bifidum* can be lyophilized. The mammal can be a human. The bacterial composition can comprises a coating that prevents release of the *Lactobacillus acidophilus, Lactobacillus plantarum, Lactobacillus casei, Lactobacillus rhamnosus, Bifidobacterium longum, Bifidobacterium lactis*, and *Bifidobacterium bifidum* until the composition reaches an intestine of the mammal following oral administration to the mammal. The bacterial composition can comprise a capsule housing the *Lactobacillus acidophilus, Lactobacillus plantarum, Lactobacillus casei, Lactobacillus rhamnosus, Bifidobacterium longum, Bifidobacterium lactis*, and *Bifidobacterium bifidum*. The composition can comprise a microcrystalline cellulose.

In another aspect, this document features a method for making a bacterial composition. The method comprises, or consists essentially of, (a) coating lyophilized bacteria with silicon dioxide to form coated lyophilized bacteria, (b) adding MCC having a water activity of less than 0.2 and fructooligosaccharides to the coated lyophilized bacteria to form a first mixture, (c) adding magnesium stearate and silicon dioxide to the first mixture to form a blend, and (d) encapsulating the blend into a dosage form, thereby forming the bacterial composition. The lyophilized bacteria can be a mixture of lyophilized *Lactobacillus acidophilus, Lactobacillus plantarum, Lactobacillus casei, Lactobacillus rhamnosus, Bifidobacterium longum, Bifidobacterium lactis*, and *Bifidobacterium bifidum*. For every gram of the composition, the composition can comprise (a) between about $4 \times 10^9$ colony forming units and about $50 \times 10^9$ colony forming units of *Lactobacillus acidophilus*; (b) between about $5 \times 10^9$ colony forming units and about $60 \times 10^9$ colony forming units of *Lactobacillus plantarum*; (c) between about $4 \times 10^9$ colony forming units and about $50 \times 10^9$ colony forming units of *Lactobacillus casei*; (d) between about $4 \times 10^9$ colony forming units and about $50 \times 10^9$ colony forming units of *Lactobacillus rhamnosus*; (e) between about $2 \times 10^9$ colony forming units and about $40 \times 10^9$ colony forming units of *Bifidobacterium longum*; (f) between about $4 \times 10^9$ colony forming units and about $50 \times 10^9$ colony forming units of *Bifidobacterium lactis*; and (g) between about $2 \times 10^9$ colony forming units and about $40 \times 10^9$ colony forming units of *Bifidobacterium bifidum*. For every gram of the composition, the composition can comprise between about 0.5 mg and about 5.0 mg of fructooligo-saccharides. For every gram of the composition, the composition can comprise between about 5.0 mg and about 20.0 mg of silicon dioxide. For every gram of the composition, the composition can comprise more than $15 \times 10^9$ CFUs of bacteria. For every gram of the composition, more than $10 \times 10^9$ CFUs of bacteria of the composition remain viable after about 12 months of storage at room temperature and environmental humidity. The dosage form can be a capsule.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides bacterial compositions. For example, this document provides bacterial compositions having a combination of different bacterial strains (e.g., a combination of at least six, seven, eight, nine, or ten different bacterial strains) formulated in a manner to maintain the stability of the bacteria. The bacterial compositions provided herein can be in the form of powders, capsules, pills, tablets, chewing gums, lozenges, candy, or sachets. In some cases, a bacterial composition provided herein can include a coating designed to prevent moisture adsorption and minimize the water activity of the final blend to provide a formulation with good long term stability.

For example, methacrylate coatings, hydroxy propyl methyl cellulose pthalate coatings, cellulose acetate succinate coatings, hydroxy propyl methyl cellulose acetate succinate coatings, polyvinyl acetate pthalate coatings, or cellulose acetate trimellitate sodium alginate coatings can be used to deliver the bacterial contents of a bacterial composition past the stomach. Such coatings can be made and applied as described elsewhere (e.g., U.S. Patent Application Publication No. 2014/370091, Chinese Patent No. CN103976975, and Taiwan Patent No. TW201431561).

In some cases, a bacterial composition provided herein can include any combination of at least six (e.g., at least seven, eight, nine, or ten) different bacterial strains. Examples of different bacterial strains that can be formulated into a bacterial composition provided herein include, without limitation, *Lactobacillus acidophilus, Lactobacillus plantarum, Lactobacillus casei, Lactobacillus rhamnosus, Bifidobacterium longum, Bifidobacterium lactis, Bifidobacterium bifidum, Bacillus coagulans, Lactobacillus paracasei, Lactobacillus johnsonii, Lactobacillus reuteri, Lactobacillus bulgaricus, Bifidobacterium breve, Lactobacillus brevis, Lactococcus lactis* and *Streptococcus thermophilus*. In some cases, a bacterial composition provided herein can include one or more bacterial species such as *Saccharomyces boulardii* In some cases, the only bacterial strains present within a particular bacterial composition can be *Lactobacillus acidophilus, Lactobacillus plantarum, Lactobacillus casei, Lactobacillus rhamnosus, Bifidobacterium longum, Bifidobacterium lactis*, and *Bifidobacterium bifidum*, or any combination of six selected from *Lactobacillus acidophilus, Lactobacillus plantarum, Lactobacillus casei, Lactobacillus rhamnosus, Bifidobacterium longum, Bifidobacterium lactis*, and *Bifidobacterium bifidum*.

Unless otherwise noted, all bacteria amounts in this application are provided on a per gram of total bacterial composition in the composition basis. In some cases, a bacterial composition provided herein can contain at least about $1 \times 10^9$ CFUs of each different bacterial strain included in the bacterial composition. In some cases, a bacterial composition provided herein can contain between about $1 \times 10^8$ and about $1 \times 10^{11}$ bacteria of all species (e.g., between about $1 \times 10^9$ and about $4 \times 10^{10}$ bacteria of all species). For example, a bacterial composition provided herein can include between about $1 \times 10^7$ CFUs and about $3 \times 10^9$ CFUs of *Lactobacillus acidophilus*, between about $1 \times 10^7$ CFUs and about $4 \times 10^9$ CFUs of *Lactobacillus plantarum*, between about $1 \times 10^7$ CFUs and about $3 \times 10^9$ CFUs of *Lactobacillus casei*, between about $1 \times 10^7$ CFUs and about $3.2 \times 10^9$ CFUs of *Lactobacillus rhamnosus*, between about $1 \times 10^7$ CFUs and about 1.6×10⁹ CFUs of *Bifidobacterium longum*, between about 1×10⁷ CFUs and about 3.6×10⁹ CFUs of *Bifidobacterium lactis*, and between about 1×10⁷ CFUs and about 1.6×10⁹ CFUs of *Bifidobacterium bifidum*.

Any appropriate method can be used to obtain the bacterial strains to be included within a bacterial composition provided herein. For example, culturing techniques can be used to obtain large amounts of particular bacterial strains. In some cases, the bacterial strains to be included within a bacterial composition provided herein can be obtained commercially. For example, *Lactobacillus acidophilus* can be obtained commercially from Dupont Inc. (Madison, Wis.; Cat. No. LA-14 200B); *Lactobacillus plantarum* can be obtained commercially from Dupont Inc. (Madison, Wis.; Cat. No. LP-115 400B); *Lactobacillus casei* can be obtained commercially from Dupont Inc. (Madison, Wis.; Cat. No. LC-11 300B), *Lactobacillus rhamnosus* can be obtained commercially from Dupont Inc. (Madison, Wis.; Cat. No. LR-32 200B), *Bifidobacterium longum* can be obtained commercially from Dupont Inc. (Madison, Wis.; Cat. No. BL-05 100B), *Bifidobacterium lactis*, can be obtained commercially from Dupont Inc. (Madison, Wis.; Cat. No. BL-04 450B), and *Bifidobacterium bifidum* can be obtained commercially from Dupont Inc. (Madison, Wis.; Cat. No. BB-06 100B).

A bacterial composition provided herein can include one or more other ingredients. For example, a bacterial composition provided herein can include fructooligosaccharides. In some cases, a bacterial composition provided herein can include between about 0.5 mg and about 50 mg (e.g., between about 1 mg and about 50 mg, between about 5 mg and about 50 mg, between about 10 mg and about 50 mg, between about 0.5 mg and about 25 mg, between about 0.5 mg and about 20 mg, between about 0.5 mg and about 15 mg, between about 0.5 mg and about 10 mg, or between about 5 mg and about 20 mg) of fructooligosaccharides per bacterial composition. For example, a bacterial composition provided herein can contain *Lactobacillus acidophilus, Lactobacillus plantarum, Lactobacillus casei, Lactobacillus rhamnosus, Bifidobacterium longum, Bifidobacterium lactis*, and *Bifidobacterium bifidum* and between about 5 mg and about 20 mg of fructooligosaccharides.

In some cases, a bacterial composition provided herein can include between about 1 mg and about 50 mg (e.g., between about 1 mg and about 20 mg, between about 2 mg and about 20 mg, or between about 2 mg and about 10 mg) of fructooligosaccharides for every gram of the bacterial composition. For example, a bacterial composition provided herein that weighs 2 grams can contain between about 10 mg and about 100 mg of fructooligosaccharides.

Any appropriate method can be used to obtain fructooligosaccharides that can be included in a bacterial composition provided herein. For example, fructooligosaccharides can be obtained by an inulin degradation process or by a transfructosylation process as described elsewhere (U.S. Patent Application Publication No. 2005/069627). In some cases, fructooligosaccharides can be obtained commercially from Agaviotica Inc. (Monterrey, NL (Mexico); Cat. No. Fructagave PR-95).

In some cases, a bacterial composition provided herein can include a glidant (e.g., silica). Examples of glidants that can be included within a bacterial composition provided herein include, without limitation, silica, stearic acid, calcium stearate, magnesium stearate, sodium stearate, glyceryl behapate (compritol), liquid paraffin, Aerosil® (colloidal silicon dioxide), starch and talc, DL-leucine, and sodium lauryl sulfate. For example, a bacterial composition provided herein can include between about 2.00 mg and about 5.00 mg (e.g., between about 0.005 mg and about 010 mg, between about 0.01 mg and about 0.02 mg, or between about 0.25 mg and about 0.50 mg) of a glidant (e.g., silica) per bacterial composition. For example, a bacterial composition provided herein can contain *Lactobacillus acidophilus, Lactobacillus plantarum, Lactobacillus casei, Lactobacillus rhamnosus, Bifidobacterium longum, Bifidobacterium lactis*, and *Bifidobacterium bifidum* and between about 0.005 mg and about 0.02 mg of silica.

In some cases, a bacterial composition provided herein can include between about 2.0 mg and about 5.0 mg of a glidant (e.g., silica) for every gram of the bacterial composition. For example, a bacterial composition provided herein that weighs 2 grams can contain between about 4.0 mg and about 10.0 mg of a glidant (e.g., silica).

Any appropriate method can be used to obtain of a glidant (e.g., silica) that can be included in a bacterial composition provided herein. For example, silica can be obtained as described elsewhere (U.S. Patent Application Publication No. 2006/153764). In some cases, silica can be obtained commercially from Grace Davison Inc. (Baltimore, Md.; Cat. No. Syloid 244).

In some cases, a bacterial composition provided herein can include a filler having an $A_w$ of less than 0.2. Examples of such fillers include, without limitation, microcrystalline cellulose (MCC 112), rice maltodextrin, lactose anhydrous, mannitol, microcrystalline cellulose (MCC 302), microcrystalline cellulose (MCC 200 LM), microcrystalline cellulose (MCC 101), starch, xylitol, sorbitol, hydroxyl propyl cellulose, a gelatin, polyvinyl pyrrolidone, and dibasic calcium phosphate. In some cases, a bacterial composition provided herein can include between about 300 mg and about 700 mg of a filler having an $A_w$ of less than 0.2 (e.g., MCC 112) per bacterial composition. For example, a bacterial composition provided herein can contain *Lactobacillus acidophilus, Lactobacillus plantarum, Lactobacillus casei, Lactobacillus rhamnosus, Bifidobacterium longum, Bifidobacterium lactis*, and *Bifidobacterium bifidum* and between about 300 mg and about 700 mg of a filler having an $A_w$ of less than 0.2 (e.g., MCC 112). In some cases, a bacterial composition provided herein can include between about 300 mg and about 700 mg of a filler having an $A_w$ of less than 0.2 (e.g., MCC 112) for every gram of the bacterial composition. For example, a bacterial composition provided herein that weighs 2 grams can contain between about 600 mg and about 1400 mg of a filler having an $A_w$ of less than 0.2 (e.g., MCC 112). As a result, the final composition can have an $A_w$ of less than 0.3.

Any appropriate method can be used to obtain a filler having an $A_w$ of less than 0.2 for use in the bacterial compositions provided herein. For example, a filler having an $A_w$ of less than 0.2 can be obtained as described elsewhere (U.S. Patent Application Publication No. US20140322282, published Oct. 30, 2014). In some cases, a filler having an $A_w$ of less than 0.2 can be obtained commercially from Mingtai chemical Co Ltd., Taiwan, Cat. No. M112 D.

In some cases, a bacterial composition provided herein can include magnesium stearate. For example, a bacterial composition provided herein can include between about 10 mg and about 20 mg of magnesium stearate per bacterial composition. For example, a bacterial composition provided herein can contain *Lactobacillus acidophilus, Lactobacillus plantarum, Lactobacillus casei, Lactobacillus rhamnosus, Bifidobacterium longum, Bifidobacterium lactis*, and *Bifidobacterium bifidum* and between about 10 mg and about 20 mg of magnesium stearate.

In some cases, a bacterial composition provided herein can include between about 10 mg and about 20 mg of magnesium stearate for every gram of the bacterial composition. For example, a bacterial composition provided herein that weighs 2 grams can contain between about 20 mg and about 40 mg of magnesium stearate.

Any appropriate method can be used to obtain magnesium stearate that can be included in a bacterial composition provided herein. For example, magnesium stearate can be obtained as described elsewhere (e.g., Chinese Patent No. CN103880645, dated Jun. 25, 2014; Chinese Patent No. CN103524324, dated Jan. 22, 2014, and Chinese Patent No. CN10319361, dated Jul. 10, 2013). In some cases, magnesium stearate can be obtained commercially from Peter Greven Asia, Malaysia; Cat. No. Palmstar MGST 200. A bacterial composition provided herein (e.g., a capsule or tablet) can be formulated to have a particular dose. For example, a bacterial composition provided herein can be in the form of a capsule or tablet with a total weight that is between about 150 mg and about 800 mg (e.g., between about 200 mg and about 800 mg, between about 300 mg and about 800 mg, between about 350 mg and about 800 mg, between about 150 mg and about 700 mg, between about 150 mg and about 650 mg, or between about 350 mg and about 700 mg).

As described herein, a single bacterial composition (e.g., a capsule or tablet) can be formulated to include at least six different bacterial strains and a filler having an $A_w$ less than 0.2 (e.g., MCC 112) in a manner that helps maintain the stability of the bacteria within the composition. In some cases, a single bacterial composition provided herein can be coated with at coating or placed into a capsule having the ability to deliver the contents to the intestines of a mammal following oral administration. For example, a bacterial composition provided herein can be designed to release its contents when the composition reaches a location of the intestines having a pH above about 6.8. In some cases, a bacterial composition that includes at least seven different bacterial strains and a filler having an $A_w$ less than 0.2 (e.g., MCC 112) can include fructooligosaccharides, magnesium stearate, and/or silica. In some cases, the bacterial strains of a bacterial composition provided herein can be lyophilized to form a dried powder containing viable bacteria. In some cases, a single bacterial composition (e.g., a capsule or tablet or sachet) can be formulated to include at least seven different lyophilized bacterial strains, a filler having an $A_w$ less than 0.2 (e.g., MCC 112), fructooligosaccharides, magnesium stearate, and silica.

In some cases, a bacterial composition provided herein can maintain the viability of at least about 80 percent (e.g. at least about 90, 95, or 99 percent) of the bacteria for at least 12 months (e.g., at least 40, 50, 60, 70, 80, or 90 days or at least 3, 6, 9, or 12 months) under standard storage conditions (e.g., room temperature under normal humidity). In some cases, a bacterial composition provided herein can maintain the viability of at least about 80 percent of the bacteria for at least 18 months or for at least 24 months.

The bacterial composition provided herein can be administered to a mammal (e.g., a human). In some cases, a human can be instructed to self-administer a number (e.g., one, two, three, four, five, or more) bacterial compositions provided herein (e.g., capsules or tablets or sachets) per unit time (e.g., per day, per week, or per month). For example, a human can be instructed to self-administer one or two bacterial compositions provided herein (e.g., a capsule of Example 1) per day.

The invention will be further described in the following examples, which do not limit the scope of the invention described in the claims.

EXAMPLES

Example 1—Stability of Bacterial Compositions

Two bacterial compositions were produced (Prototype trial 1 and Prototype trial 2) as follows. The final formulations were stored in various bottles as described below:

(i) MCC 101 and MCC 112 were used as diluent in prototype trials.

(ii) PET bottle, HDPE bottle, and sealed Aluminum foil packet were used in storing the final capsule.

Prototype trial 1:

| Component | Potency of raw ingredient (billion CFU/g) | % of ingredients | Final Potency (Billion CFU/g) |
|---|---|---|---|
| Lactobacillus acidophilus | 200 | 7.58 | 15.00 |
| Bifidobacterium lactis | 450 | 2.07 | 9.00 |
| Fructooligosaccharides | | 3.70 | |
| Dicalcium Phosphate | | 1.85 | |
| MCC 101 | | 81.90 | |
| Calcium Stearate | | 1.40 | |
| Silicon Dioxide | | 1.48 | |
| Total | | 100.0% | 24 |

270 mg of above blend was filled into a single capsule.
Potency of 270 mg of blend=24/1000*270=6.48 billion CFUs/capsule Prototype trial 2:

| Component | Potency of raw ingredient (billion CFU/g) | % of ingredients | Final Potency (Billion CFU/g) |
|---|---|---|---|
| Lactobacillus acidophilus | 200 | 7.58 | 15.00 |
| Bifidobacterium lactis | 450 | 2.07 | 9.00 |
| Fructooligosaccharides | | 3.70 | |
| MCC 112 | | 83.75 | |
| Calcium Stearate | | 1.40 | |
| Silicon Dioxide | | 1.48 | |
| Total | | 100.0% | 24 |

270 mg of above blend was filled into a single capsule.
Potency of 270 mg of blend=24/1000*270=6.48 billion CFUs/capsule Prototype trial 3 is made as follows:

| Component | Potency of raw ingredient (billion CFUs/g) | % of ingredients | Final Potency (Billion CFU/g) |
|---|---|---|---|
| Lactobacillus acidophilus | 200 | 7.58 | 15.00 |
| Bifidobacterium lactis | 450 | 2.07 | 9.00 |
| Fructooligosaccharides | | 3.70 | |
| Dicalcium Phosphate | | 1.85 | |
| MCC 112 | | 81.90 | |
| Calcium Stearate | | 1.40 | |
| Silicon Dioxide | | 1.48 | |
| Total | | 100.0% | 24 |

| Component | Potency of raw ingredient (billion CFUs/g) | % of ingredients | Final Potency (Billion CFU/g) |
|---|---|---|---|

270 mg of above blend is used to fill a single capsule.
Potency of 270 mg of blend=24/1000*270=6.48 billion CFUs/capsule Once produced, the two bacterial compositions were tested for stability (Table 1).

TABLE 1

Probiotics count (CFUs/capsule) and water activity.

| | Formulation filler | | | |
|---|---|---|---|---|
| | MCC 101 | MCC 112 | MCC 112 | MCC 112 |
| | | Packaging type | | |
| | PET (Polyethylene terephthalate) bottle | PET bottle | High Density Polyethylene (HDPE) bottle | Aluminum foil packet |
| | CFU/capsule / $A_w$ | CFU/capsule / $A_w$ | CFU/capsule / $A_w$ | CFU/capsule / $A_w$ |
| Initial | 7.3 billion / NA | 5.4 billion / 0.165 | 5.0 billion / 0.130 | 5.8 billion / 0.130 |
| after 3 months at 25° C./60 relative humidity | NA / NA | 8.4 billion / 0.169 | 8.4 billion / 0.133 | 8.1 billion / 0.141 |
| after 3 months at 30° C./75 relative humidity | 0.0016 billion / NA | 2.9 billion / 0.171 | 8.7 billion / 0.125 | 7.8 billion / 0.141 |

These results demonstrate that, using microcrystalline cellulose in bacterial compositions having at least two strains, MCC 112 improved stability over MCC 101 and that using a High Density Polyethylene (HDPE) bottle or Aluminum foil packet improved stability over using a PET bottle.

Example 2—Stability of Bacterial Compositions

A bacterial composition was produced as follows.

| Component | Potency of strain | % of ingredients, by weight | Final Potency in Billion CFU |
|---|---|---|---|
| Lactobacillus acidophilus | 200 | 3.75 | 7.5 |
| Lactobacillus plantarum | 400 | 2.5 | 10 |
| Lactobacillus casei | 300 | 2.5 | 7.5 |
| Lactobacillus rhamnosus | 200 | 4.0 | 8.0 |
| Bifidobacterium longum | 100 | 4.0 | 4.0 |
| Bifidobacterium lactis | 450 | 2.0 | 9.0 |
| Bifidobacterium bifidum | 100 | 4.0 | 4.0 |
| Fructooligosaccharides | | 5.0 | |
| MCC 112 | | 70.25 | |
| Magnesium Stearate (Palmstar MGST 325) | | 1.50 | |
| Silicon Dioxide (Syloid 244) | | 0.50 | |
| Total | | 100.0% | 50 |

400 mg of the above blend was filled into a single DR capsule. The potency of the 400 mg of blend was 20 billion CFUs/capsule.

Once produced, the bacterial composition was tested for stability (Table 2).

TABLE 2

Probiotics count (CFUs/capsule) and water activity.

| | |
|---|---|
| Formulation filler | MCC 112 |
| Bottle type | HOPE |
| Initial CFUs/capsule | 12.7 billion |
| Initial water activity ($A_w$) | 0.139 |
| CFUs/capsule after 3 months at 25° C./60 relative humidity | 14.0 billion |

TABLE 2-continued

Probiotics count (CFUs/capsule) and water activity.

| | |
|---|---|
| Water activity ($A_w$) after 3 months at 25° C./60 relative humidity | 0.133 |

These results confirm that using microcrystalline cellulose MCC 112 and a High Density Polyethylene (HDPE) bottle maintained stability in a bacterial composition having seven strains of bacteria.

Example 3—Bacterial Composition

A bacterial composition was prepared as follows (Table 3). Briefly, lyophilized bacteria of varying CFUs of each of Lactobacillus acidophilus, Lactobacillus plantarum, Lactobacillus casei, Lactobacillus rhamnosus, Bifidobacterium longum, Bifidobacterium lactis, and Bifidobacterium bifidum and silicon dioxide (silica; 2 mg) were blended for two minutes to coat the dried bacteria uniformly. The silica can adsorb moisture, keeping the lyophilized bacteria dry with minimal water activity and improving the stability of final formulation. MCC 112 (grade of microcrystalline cellulose with $A_w$ of less than 0.2 (700 mg), and fructooligosaccharides (50 mg) were then added, and the mixture was blended for an additional 20 minutes. After blending, additional silica (3 mg) as a glidant and magnesium stearate (15 mg) as lubricant, were added, and the mixture was blended for another three minutes. The final mixture was inserted into capsules (e.g., DR capsules). DR capsules are vegetarian capsules made with a hypromellose (HPMC) formulation that can help protect sensitive ingredients from the low pH environment of the stomach. By protecting against early disintegration, disintegration generally starts approximately 45 minutes later than a typical immediate release capsule of about 5 minutes, and the ingredients are released in the intestine in alkaline pH.

TABLE 3

Bacterial composition.

| Component | raw ingr. level (billion CFUs/g) | example formula 1 % of ingr., by weight | example formula 1 finished product (billion CFUs/g) | example formula 2 % of ingr., by weight | example formula 2 finished product (billion CFUs/g) | example formula 3 % of ingr., by weight | example formula 3 finished product (billion CFUs/g) | example formula 4 % of ingr., by weight | example formula 4 finished product (billion CFUs/g) | example formula 5 % of ingr., by weight | example formula 5 finished product (billion CFUs/g) |
|---|---|---|---|---|---|---|---|---|---|---|---|
| *Lactobacillus acidophilus* | 200 | 3.75% | 7.5 | 3.75% | 7.5 | 3.75% | 7.5 | 7.50% | 15.0 | 7.50% | 15 |
| *Lactobacillus plantarum* | 400 | 2.50% | 10 | 2.50% | 10 | 2.50% | 10 | 1.00% | 4.0 | 2.00% | 8 |
| *Lactobacillus casei* | 300 | 2.50% | 7.5 | 2.50% | 7.5 | 2.50% | 7.5 | 1.80% | 5.40 | 0.90% | 2.7 |
| *Lactobacillus rhamnosus* | 200 | 4.00% | 8 | 4.00% | 8 | 4.00% | 8 | 0.90% | 1.80 | 0.90% | 1.8 |
| *Bifidobacterium longum* | 100 | 4.00% | 4 | 4.00% | 4 | 4.00% | 4 | 1.00% | 1.00 | 0.10% | 0.1 |
| *Bifidobacterium lactis* | 450 | 2.00% | 9 | 2.00% | 9 | 2.00% | 9 | 15.00% | 67.5 | 7.50% | 33.75 |
| *Bifidobacterium bifidum* | 100 | 4.00% | 4 | 4.00% | 4 | 4.00% | 4 | 0.20% | 0.20 | 0.10% | 0.1 |
| Fructooligo-saccharides | | 5.00% | | 5.00% | | 5.00% | | 5.00% | | 5.00% | |
| MCC 112 | | 70.25% | | | | | | | | | |
| MCC 101 | | | | | | 30 | | 65.6 | | | |
| MCC 302 | | | | | | | | | | 74% | |
| Rice Maltodextrin | | | | 70.25 | | 40.25 | | | | | |
| Magnesium Stearate (Palmstar MGST 325) | | 1.50% | | 1.00% | | 0.75% | | 1.5% | | | |
| Calcium Stearate | | | | 0.25 | | 0.5 | | | | 1.50% | |
| colloidal silicon dioxide (AEROSIL ® R 972 Pharma) | | | | | | | | 0.25% | | | |
| Silicon Dioxide (Syloid 244) | | 0.50% | | 0.75% | | 0.75% | | 0.25 | | 0.50% | |
| Total | | 100% | 50 | | | | | 100.0 | 94.9 | 100% | 61.45 |

Ingr. = ingredient

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A bacterial composition comprising *Lactobacillus acidophilus, Lactobacillus plantarum, Lactobacillus casei, Lactobacillus rhamnosus, Lactobacillus paracasei,* and *Bifidobacterium lactis,* wherein said bacterial composition is effective to release said *Lactobacillus acidophilus, Lactobacillus plantarum, Lactobacillus casei, Lactobacillus rhamnosus,* *Lactobacillus paracasei,* and *Bifidobacterium lactis,* within an intestine of a mammal following oral administration to said mammal;

wherein said composition comprises microcrystalline cellulose (MCC) and has a water activity of about 0.125 to about 0.3; and wherein said bacterial composition comprises a uniform silicon dioxide coating that reduces moisture absorption by said *Lactobacillus acidophilus, Lactobacillus plantarum, Lactobacillus casei, Lactobacillus rhamnosus, Lactobacillus paracasei,* and *Bifidobacterium lactis* prior to oral administration to said mammal.

2. The composition of claim 1, wherein for every gram of the composition said composition comprises between about $4 \times 10^9$ colony forming units and about $50 \times 10^9$ colony forming units of *Lactobacillus acidophilus.*

3. The composition of claim 1, wherein for every gram of the composition said composition comprises between about $5 \times 10^9$ colony forming units and about $60 \times 10^9$ colony forming units of *Lactobacillus plantarum.*

4. The composition of claim 1, wherein for every gram of the composition said composition comprises between about $4 \times 10^9$ colony forming units and about $50 \times 10^9$ colony forming units of *Lactobacillus casei.*

5. The composition of claim 1, wherein for every gram of the composition said composition comprises between about $4\times10^9$ colony forming units and about $50\times10^9$ colony forming units of *Lactobacillus rhamnosus*.

6. The composition of claim 1, wherein for every gram of the composition said composition comprises at least about $1\times10^9$ colony forming units of *Lactobacillus paracasei*.

7. The composition of claim 1, wherein for every gram of the composition said composition comprises between about $4\times10^9$ colony forming units and about $50\times10^9$ colony forming units of *Bifidobacterium lactis*.

8. The composition of claim 1, wherein said MCC is MCC grade 112.

9. The composition of claim 1, wherein said composition comprises fructooligosaccharides.

10. The composition of claim 8, wherein for every gram of the composition said composition comprises between about 0.5 mg and about 50 mg of fructooligosaccharides.

11. The composition of claim 1, wherein for every gram of composition said composition comprises between about 5 mg and about 20 mg of silicon dioxide.

12. The composition of claim 1, wherein said composition comprises magnesium stearate.

13. The composition of claim 1, wherein for every gram of composition, said composition comprises between about 10 mg and about 20 mg of magnesium stearate.

14. The composition of claim 1, wherein for every gram of the composition said composition comprises more than $8\times10^9$ CFUs of bacteria.

15. The composition of claim 1, wherein for every gram of the composition said composition comprises more than $10\times10^9$ CFUs of bacteria.

16. The composition of claim 1, wherein for every gram of the composition said composition comprises more than $15\times10^9$ CFUs of bacteria.

17. The composition of claim 16, wherein for every gram of the composition more than $10\times10^9$ CFUs of bacteria of said composition remain viable after about 12 months of storage at room temperature and environmental humidity.

18. The composition of claim 16, wherein for every gram of the composition more than $10\times10^9$ CFUs of bacteria of said composition remain viable after about 12 months of storage at room temperature and environmental humidity.

19. The composition of claim 1, wherein said mammal is a human.

20. The composition of claim 1, wherein said composition has a water activity of about 0.13 to about 0.3.

21. The composition of claim 1, wherein said composition includes the MCC in an amount of about 300 mg to about 700 mg for every gram of the composition.

22. The composition of claim 1, wherein said composition is effective to release its contents when the composition reaches a location of the intestines having a pH above about 6.8.

23. A method for making a bacterial composition, wherein said method comprises:
(a) coating lyophilized bacteria to form coated lyophilized bacteria having a uniform silicon dioxide coating, wherein the bacteria comprise *Lactobacillus acidophilus, Lactobacillus plantarum, Lactobacillus casei, Lactobacillus rhamnosus, Lactobacillus paracasei*, and *Bifidobacterium lactis*,
(b) adding MCC having a water activity of less than 0.3 and fructooligosaccharides to said coated lyophilized bacteria to form a mixture, wherein said mixture has a water activity of about 0.125 to about 0.3, and
(c) encapsulating said mixture into a capsule, thereby forming said bacterial composition, wherein said capsule is effective to release said *Lactobacillus acidophilus, Lactobacillus plantarum, Lactobacillus casei, Lactobacillus rhamnosus, Lactobacillus paracasei*, and *Bifidobacterium lactis* within an intestine of a mammal following oral administration to said mammal.

24. The method of claim 23, wherein said MCC is MCC grade 112.

25. A bacterial composition comprising lyophilized bacteria having a uniform silicon dioxide coating, wherein said lyophilized bacteria is a mixture of lyophilized *Lactobacillus acidophilus, Lactobacillus plantarum, Lactobacillus casei, Lactobacillus rhamnosus, Lactobacillus paracasei*, and *Bifidobacterium lactis;*
wherein said bacterial composition is in the form of a capsule effective to release said *Lactobacillus acidophilus, Lactobacillus plantarum, Lactobacillus casei, Lactobacillus rhamnosus, Lactobacillus paracasei*, and *Bifidobacterium lactis* within an intestine of a mammal following oral administration to said mammal;
wherein said composition has a water activity of about 0.125 to about 0.3, and
wherein said the bacterial composition comprises MCC.

26. The composition of claim 25, wherein said silicon dioxide coating is configured to reduce moisture absorption by said *Lactobacillus acidophilus, Lactobacillus plantarum, Lactobacillus casei, Lactobacillus rhamnosus, Lactobacillus paracasei*, and *Bifidobacterium lactis* prior to oral administration to said mammal.

27. The composition of claim 25, wherein said MCC is MCC grade 112.

28. A bacterial composition comprising:
(a) lyophilized *Lactobacillus acidophilus, Lactobacillus plantarum, Lactobacillus casei, Lactobacillus rhamnosus, Lactobacillus paracasei*, and *Bifidobacterium lactis,*
(b) fructooligosaccharides, and
(c) MCC in an amount of about 300 mg to about 700 mg for every gram of the composition;
wherein said bacterial composition is in the form of a capsule effective to, following oral administration to a mammal, release said *Lactobacillus acidophilus, Lactobacillus plantarum, Lactobacillus casei, Lactobacillus rhamnosus, Lactobacillus paracasei*, and *Bifidobacterium lactis* within an intestine of said mammal when the composition reaches a location of the intestine having a pH above about 6.8;
wherein said composition has a water activity of about 0.13 to about 0.3; and
wherein said bacterial composition comprises a uniform silicon dioxide coating that reduces moisture absorption by said *Lactobacillus acidophilus, Lactobacillus plantarum, Lactobacillus casei, Lactobacillus rhamnosus, Lactobacillus paracasei*, and *Bifidobacterium lactis* prior to oral administration to said mammal.

29. The composition of claim 28, wherein said MCC is MCC grade 112.

* * * * *